United States Patent
Messenger

(10) Patent No.: US 10,232,340 B2
(45) Date of Patent: *Mar. 19, 2019

(54) SYSTEM AND METHOD FOR PH CONTROL OF LEAN MEG PRODUCT FROM MEG REGENERATION AND RECLAMATION PACKAGES

(71) Applicant: Cameron Solutions, Inc., Houston, TX (US)

(72) Inventor: Brian E. Messenger, Hook (GB)

(73) Assignee: Cameron Solutions, Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/700,859

(22) Filed: Sep. 11, 2017

(65) Prior Publication Data

US 2017/0368529 A1    Dec. 28, 2017

Related U.S. Application Data

(60) Continuation of application No. 14/973,443, filed on Dec. 17, 2015, now Pat. No. 9,757,708, which is a division of application No. 14/500,295, filed on Sep. 29, 2014, now Pat. No. 9,216,934.

(51) Int. Cl.
*B01J 19/24* (2006.01)
*C09K 8/52* (2006.01)
(Continued)

(52) U.S. Cl.
CPC .......... *B01J 19/24* (2013.01); *B01D 53/1425* (2013.01); *B01D 53/263* (2013.01); *C07C 29/88* (2013.01); *C07C 29/94* (2013.01); *C09K 8/52* (2013.01); *B01D 2252/2023* (2013.01); *B01D 2257/80* (2013.01); *B01J 2219/00177* (2013.01); *B01J 2219/24* (2013.01); *C09K 2109/00* (2013.01); *C09K 2208/22* (2013.01)

(58) Field of Classification Search
None
See application file for complete search history.

(56) References Cited

U.S. PATENT DOCUMENTS 3,474,597 A   10/1969   Eckert
5,376,343 A   12/1994   Fouche
(Continued)

FOREIGN PATENT DOCUMENTS

WO   2010036436   4/2010
WO   2010080038   7/2010
WO   2013000896   1/2013

OTHER PUBLICATIONS

Database CAPLUS in STN, Acc. No. 2012:1862384, Kaasa, WO 2012171554 A1 (Dec. 20, 2012 (abstract).
(Continued)

*Primary Examiner* — Donald R Spamer
(74) *Attorney, Agent, or Firm* — Hauptman Ham, LLP

(57) ABSTRACT

A MEG stream having a first pH level is contacted with a $CO_2$-rich gas stream to yield a MEG product having a second different and lower pH level. The system and method can be readily incorporated into a slipstream MEG recovery package, with a source of the MEG stream being a MEG regeneration section of the package. The $CO_2$-rich gas could be a vented $CO_2$ stream from the MEG reclamation section of the package. Unlike hydrochloric and acetic acid overdosing, $CO_2$ overdosing of the lean MEG stream does not lead to rapid acidification of the MEG product to be stored or injected.

21 Claims, 3 Drawing Sheets

(51) Int. Cl.
  *C07C 29/88* (2006.01)
  *C07C 29/94* (2006.01)
  *B01D 53/14* (2006.01)
  *B01D 53/26* (2006.01)
  *C09K 109/00* (2006.01)

(56) References Cited

U.S. PATENT DOCUMENTS

| | | |
|---|---|---|
| 7,994,374 B2 | 8/2011 | Talley et al. |
| 2012/0018293 A1 | 1/2012 | Kaasa et al. |
| 2015/0008190 A1 | 1/2015 | Moen et al. |

OTHER PUBLICATIONS

Database CAPLUS in STN, Acc. No. 2013:1473466 Baraka-Lokmane et al., WIT Transaction on Engineering Sciences (2013), 79 (Computational Methods in Multiphase Flow VII), pp. 511-522 (abstract).

Kristian Sandengen, "Prediction of Mineral Scale Formation in Wet Gas Condensate Pipelines and in MEG Regeneration Plants", Doctoral Thesis for the degree of philosophiae doctor, Sep. 2006, Trondheim, NTNU.

Wikepedia, "Gas Reinjection", Technolgy Stubs, Petroleum production, Mar. 2013, available online at: https://en.wikipedia.org/w/index.php?title=Gas_reinjection&oldid=543842328.

WIPO, "International Search Report and Written Opinion of the International Searching Authority", dated Nov. 9, 2015.

SYSTEM AND METHOD FOR PH CONTROL OF LEAN MEG PRODUCT FROM MEG REGENERATION AND RECLAMATION PACKAGES

CROSS-REFERENCE TO RELATED APPLICATIONS

This application is a continuation application which claims priority to U.S. patent application Ser. No. 14/973,443, filed Dec. 17, 2015, which was a divisional application that claimed priority to U.S. patent application Ser. No. 14/500,295 filed on Sep. 29, 2014, U.S. Pat. No. 9,216,934, all of which are incorporated herein by reference.

BACKGROUND

Slipstream MEG recovery packages use a regeneration section to remove water from an incoming rich MEG feed stream and produce a lean MEG stream. A portion of this lean MEG stream is routed to a reclamation unit or section where the salt component is removed to yield a salt-free, pH neutral, lean MEG stream. This salt-free lean MEG stream is then blended with the remaining lean MEG stream to produce a lean MEG product having up to 3 wt % dissolved salts and available for re-injection into the gas production line as hydrate inhibitor.

For gas fields where significant quantities of calcium and other divalent cations are present in the formation water, a calcium removal unit or section is located upstream of the regeneration section. The calcium is removed from the rich MEG stream by elevating the pH through the addition of sodium or potassium carbonates, hydroxides, or some combination thereof. The lean MEG exits the calcium removal section with an elevated pH, typically above 9.5.

Because carbonate and hydroxide are often added in excess of the required stoichiometric quantity, un-reacted carbonate and hydroxide is carried through the regeneration system and into the lean MEG product. Removal of water from the rich MEG in the regeneration section further elevates the pH of the lean MEG product sent for reinjection. Mixing this high pH lean MEG with the calcium-rich formation water in the gas production pipeline can lead to increased scaling of the pipeline by precipitation of, for example, calcium carbonate.

Therefore, a need exists to reduce the pH of the lean MEG product prior to injection and, in turn, mitigate pipeline scaling. Acidification of the lean MEG with hydrochloric acid (HCl) is an option but overdosing with hydrochloric acid can lead to rapid reduction in pH to levels at which corrosion of carbon steel pipework and vessels may occur.

SUMMARY

A lean MEG stream having a first pH level (e.g., pH>9.5) is contacted with a $CO_2$-rich gas stream to yield a lean MEG product having a second different pH level, which may be in a range of 6.5 to 7.0. The $CO_2$-rich gas could be a vented $CO_2$ stream from a MEG reclamation unit.

Carbon dioxide has advantages to hydrochloric acid (HCl) and acetic acid ($CH_3CO_2H$) for pH control because overdosing with $CO_2$—i.e., adding it in excess of the required stoichiometric quantity—does not lead to the reduction in pH observed with hydrochloric acid or the accumulation of acetates observed with acetic acid.

Embodiments of this disclosure may reduce the pH of lean MEG product prior to injection, mitigate the potential for pipeline scaling, reduce or eliminate use of dosing with organic or inorganic acids to control the pH of the lean MEG product, may be less sensitive to overdosing conditions, and does not cause rapid reduction in pH levels when an overdose condition occurs.

BRIEF DESCRIPTION OF THE DRAWINGS

So that the manner in which the above recited features can be understood in detail, a more particular description may be had by reference to embodiments, some of which are illustrated in the appended drawings, wherein like reference numerals denote like elements. It is to be noted, however, that the appended drawings illustrate various embodiments and are therefore not to be considered limiting of its scope, and may admit to other equally effective embodiments.

ELEMENTS AND NUMBERING USED IN THE DRAWINGS

Figure 1:
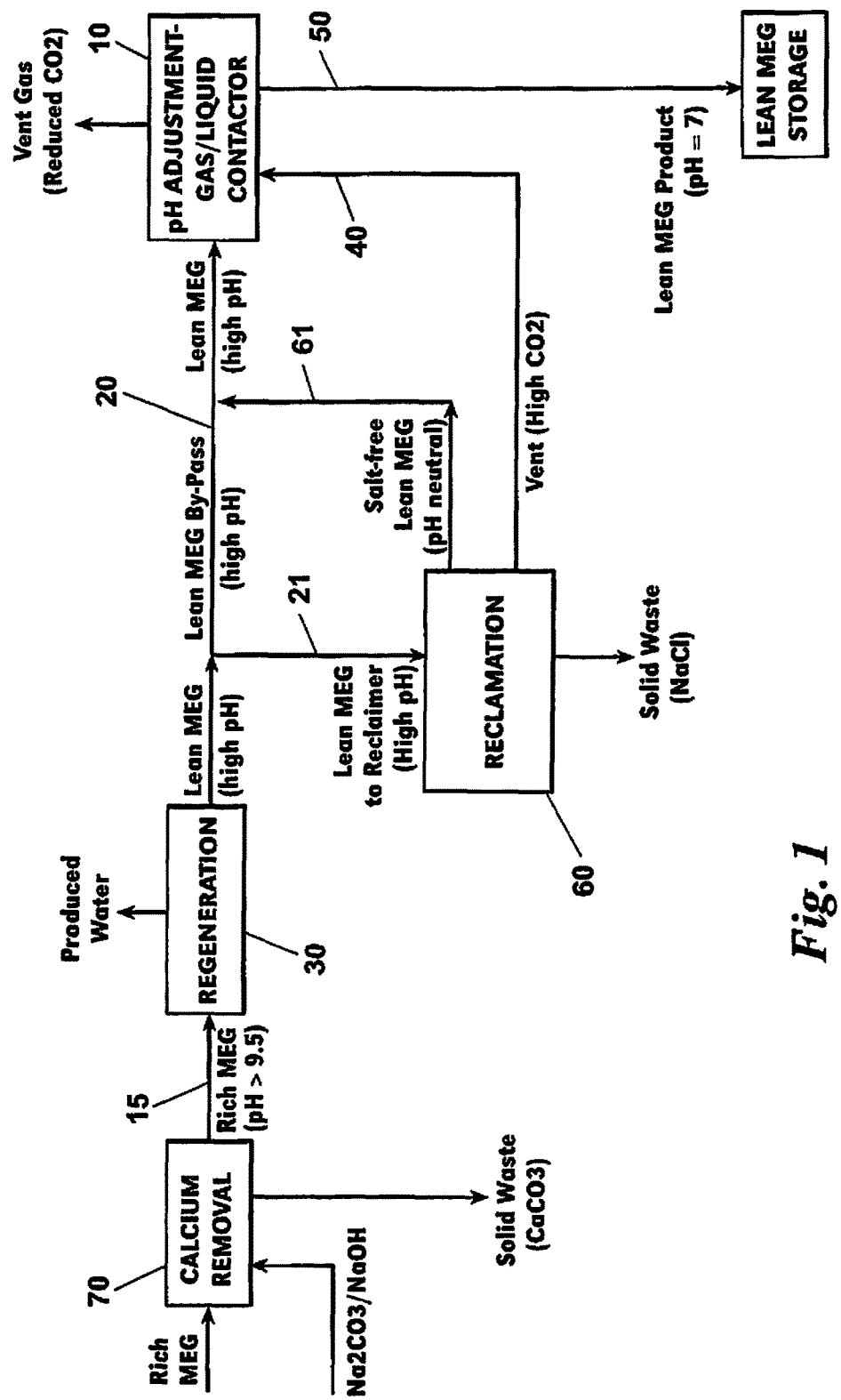
FIG. 1 is a schematic of an embodiment of a system and method of this disclosure. A vessel located downstream of a MEG regeneration section receives a high pH lean MEG stream and allows the steam to come into contact with a $CO_2$-rich gas.

10 Vessel
15 Rich MEG steam (untreated stream)
20 Lean MEG stream (treated stream)
21 Portion of lean MEG stream 20
30 MEG regeneration unit or section
$CO_2$-rich gas 40
Lean MEG product exiting 10
60 MEG reclamation unit or section
61 Salt-free lean MEG stream
70 Calcium removal unit or section

DETAILED DESCRIPTION

In the following description, numerous details are set forth to provide an understanding of some embodiments of the present disclosure. However, it will be understood by those of ordinary skill in the art that the system and/or methodology may be practiced without these details and that numerous variations or modifications from the described embodiments may be possible.

In the specification and appended claims: the terms "connect", "connection", "connected", "in connection with", and "connecting" are used to mean "in direct connection with" or "in connection with via one or more elements"; and the term "set" is used to mean "one element" or "more than one element". Further, the terms "couple", "coupling", "coupled", "coupled together", and "coupled with" are used to mean "directly coupled together" or "coupled together via one or more elements". As used herein, the terms "up" and "down", "upper" and "lower", "upwardly" and "downwardly", "upstream" and "downstream"; "above" and "below"; and other like terms indicating relative positions above or below a given point or element are used in this description to more clearly describe some embodiments of the disclosure.

Referring to FIG. 1, an embodiment of a system and method for adjusting a pH level of a lean MEG (treated) steam includes a vessel 10 which receives a lean MEG stream 20 from a lean MEG source such as a regeneration unit or section 30 of a slipstream MEG recovery package. Typically, stream 20 has a pH level above 9.5, as does rich MEG (untreated) stream 15 upstream of the regeneration section 30. Within vessel 10, this high pH lean MEG stream 20 comes into contact with a $CO_2$-rich gas 40 (i.e., greater than 50% $CO_2$ content). Vessel 10 can be a contactor vessel of a kind known in the art.

The $CO_2$ in gas 40 forms acidic solutions when dissolved in the MEG-water mixture of stream 20, thereby reducing the pH. A lean MEG product 50 having a second lower pH exits the vessel 10. In embodiments, product 50 may have a pH level of 6.5 to 7. No inorganic acids such as HCl or organic acids such as acetic or citric acid are used for reducing the pH to this level.

The $CO_2$-rich gas 40 can be from any source but, in some embodiments, is a vent stream from a reclamation unit or section 60 of the slipstream MEG recovery package. Similar to MEG regeneration section 30, MEG reclamation section 60 is of a kind well-known in the art.

A salt-free lean MEG stream 61 which exits the reclamation section 60 can be mixed with the lean MEG stream 20 prior to stream 20 entering vessel 10. Additionally, a portion 21 of the lean MEG stream 20 which exits the regeneration section 30 can be routed to the reclamation unit 60.

In slipstream MEG recovery packages that make use of a calcium removal unit or section 70 upstream of the regeneration unit 30, excess carbonate that finds its way into the reclamation section 60 degrades to form $CO_2$ (and hydroxide) under the elevated temperature, low pressure regime of a flash separator (not shown).

Figure 2:
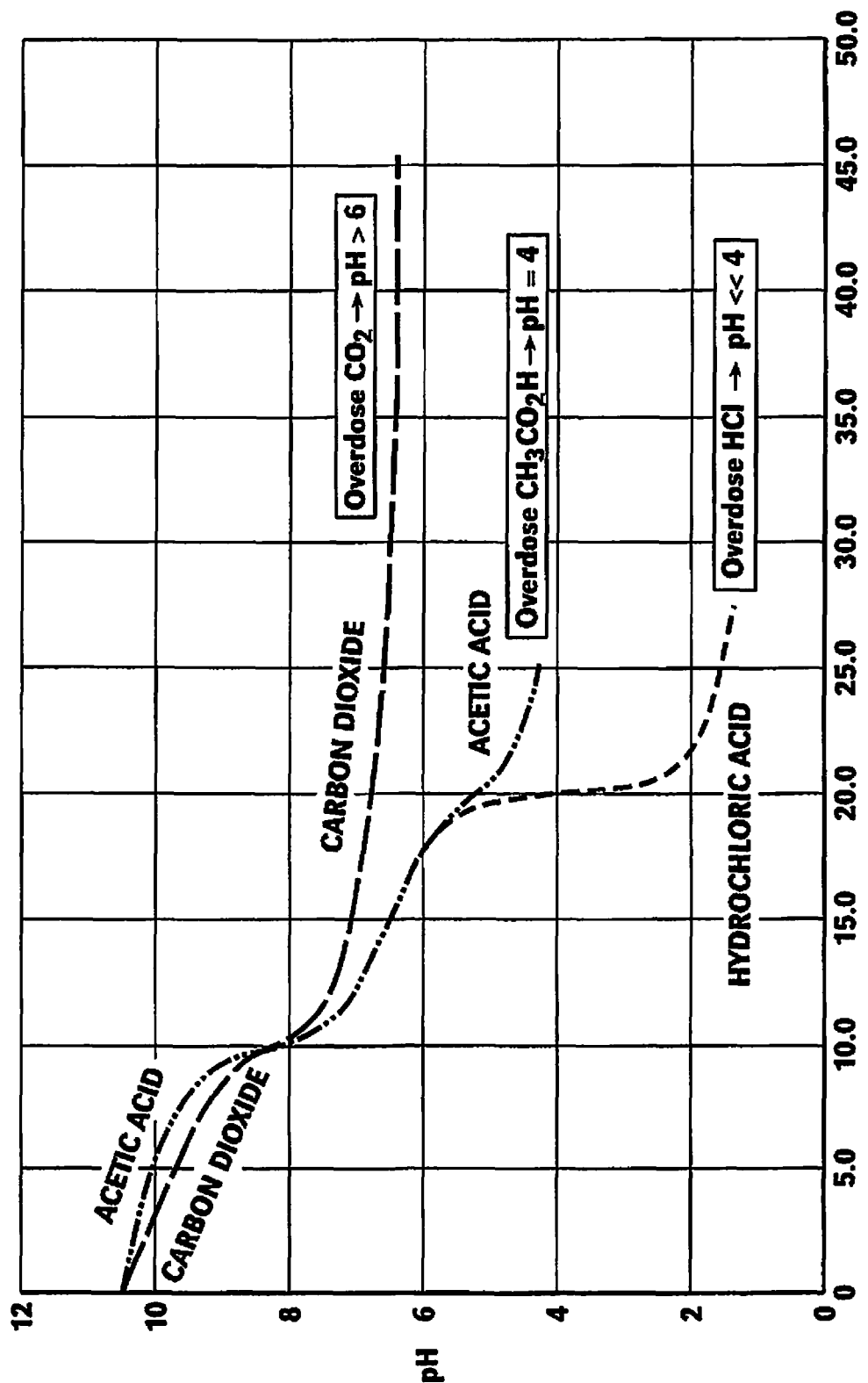
FIG. 2 is a graph illustrating a lean MEG stream with alkalinity present as sodium carbonate as the stream is treated with $CO_2$, acetic acid, and hydrochloric acid.
Figure 3:
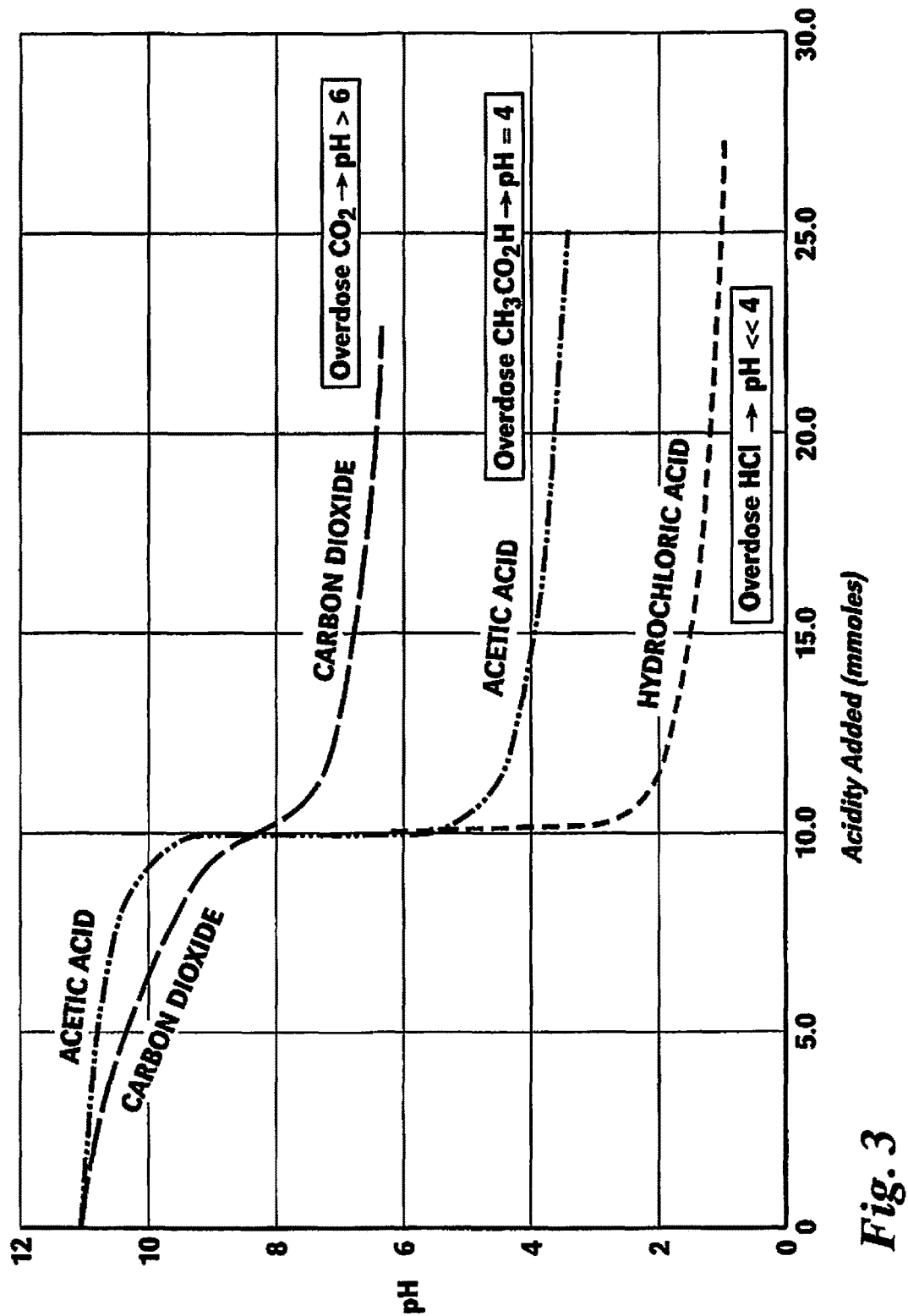
FIG. 3 is a graph illustrating a lean MEG stream with alkalinity present as sodium hydroxide as the stream is treated with $CO_2$, acetic acid, and hydrochloric acid.

Referring to FIGS. 2 and 3, unlike hydrochloric and acetic acid overdosing, $CO_2$ overdosing within vessel 10 does not lead to rapid acidification of the lean MEG product 50. In a $CO_2$ overdosing condition, the pH level remains above 6 whereas in an acetic acid and hydrochloric acid overdosing condition the pH level falls below 4 and 2 respectively. Therefore, the system and method of this disclosure is less sensitive to overdosing conditions than prior art methods.

As mentioned above, acidification with $CO_2$ removes the risk which occurs with inorganic acids (HCl) and the absence of carboxylates (acetate), namely, overdosing to the point of potentially damaging pH levels. In addition, carboxylates are highly soluble in MEG and are difficult to remove once added to the MEG system. The accumulation of carboxylates can lead to operational problems as the density and viscosity of the MEG increases with increasing carboxylate content. Hydrochloric acid converts readily to salt plus water; carbon dioxide converts to bicarbonate which is much more easily managed in the MEG system than carboxylates. Although the $CO_2$ reduces the pH, the 'alkalinity' (OH— plus $HCO_3$— plus $CO_2$) is not reduced.

To examine the "scaling" potential for the system and method, the following software simulation was run employing OLI Analyzer v 9.1.5 (OLI Systems, Inc., Cedar Knolls, N.J.).

Starting solution: 90 wt % MEG (on salt-free basis) at 40° C. containing 30,000 $mg/kg_{solvent}$ sodium chloride, 250 $mg/kg_{solvent}$ of sodium carbonate and 25 $mg/kg_{solvent}$ of sodium hydroxide. The pH of this mixture was 10.053 or about 10 (see Table 1, col. A, below).

Acidification: The MEG solution was neutralized to pH=7.0 and to pH=6.5 using HCl acetic acid and $CO_2$. Quantities of HCl, $CH_3CO_2H$ and $CO_2$ added are shown in Table 1, rows 12-14, below.

Scaling Test: Scaling potential of the acidified solutions was determined by adding in separate simulations $MgCl_2$, $CaCl_2$, $FeCl_2$, $SrCl_2$ and $BaCl_2$ to the lean MEG solutions at the quantities shown in Table 1, rows 19-23.

TABLE 1

Software Simulation of Scaling Potential.

| 1 | | | A | B | C | D | E | F | G |
|---|---|---|---|---|---|---|---|---|---|
| 2 | | | | | | | | | |
| 3 | TEMP | | 40 | 40 | 40 | 40 | 40 | 40 | 40 |
| 4 | | | | | | | | | |
| 5 | H2O | g | 100,000 | 100,000 | 100,000 | 100,000 | 100,000 | 100,000 | 100,000 |
| 6 | MEG | g | 900,000 | 900,000 | 900,000 | 900,000 | 900,000 | 900,000 | 900,000 |
| 7 | NaCl | g | 30,000 | 30,000 | 30,000 | 30,000 | 30,000 | 30,000 | 30,000 |
| 8 | Na2CO3 | g | 250 | 250 | 250 | 250 | 250 | 250 | 250 |
| 9 | NaOH | g | 25 | 25 | 25 | 25 | 25 | 25 | 25 |
| 10 | | | | | | | | | |
| 11 | ACIDIFICATION | | | | | | | | |
| 12 | HCl | g | 0 | 136 | — | — | 160 | — | — |
| 13 | CHCO2H | g | 0 | — | 228 | — | — | 279 | — |
| 14 | CO2 | g | 0 | — | — | 239 | — | — | 478 |
| 15 | | | | | | | | | |
| 16 | pH | — | 10.05 | 7.01 | 7.01 | 7.01 | 6.50 | 6.50 | 6.50 |
| 17 | | | | | | | | | |
| 18 | SCALING TEST POST ACIDIFICATION | | | | | | | | |
| 19 | MgCl2 for Mg precipitation as Mg(OH)2 | g | | | | | | | |
| 20 | CaCl2 for Ca precipitation as CaCO3 | g | 1.4 | 840 | 880 | 250 | 4300 | 5300 | 800 |
| 21 | FeCl2 for Fe precipitation as FeCO3 | g | 0.1 | 1.5 | 1.7 | 0.8 | 6.7 | 7.7 | 2.4 |
| 22 | SrCl2 for Sr precipitation as SrCO3 | g | 0.5 | 650 | 660 | 200 | 3900 | 3950 | 620 |
| 23 | BaCl2 for Ba precipitation as BaCO3 | g | 0.2 | 7 | 13.7 | 2.1 | 35 | 80 | 6.3 |

Results: For the starting solution (col. A, pH=10.0) precipitation of divalent cations as carbonate occurs on addition of 1.4 g of $CaCl_2$. After acidification to pH 7.0 with HCl, the quantity of calcium chloride added before precipitation of $CaCO_3$ increases to 840 g from 1.4 g. The effect with acetic acid is similar with precipitation starting at 880 g of $CaCl_2$. The equivalent scaling point with carbon dioxide occurs at 250 g, less than that for HCl or acetic acid but a considerable improvement on the 1.4 g for the untreated sample.

Similar trends are observed for the other divalent cations (Fe, Sr, Ba) although some are more insoluble than others. Iron, in particular, tends to precipitate out readily. At pH=6.5 (col. E-G) the trends agree with those shown at pH=7.0 (col. B-D), i.e. precipitation of divalent cations (Ca, Fe, Sr, and Ba) from the lean MEG is inhibited by addition of $CO_2$ to the alkaline lean MEG mixture.

Although the preceding description has been described herein with reference to particular means, materials and embodiments, it is not intended to be limited to the particulars disclosed herein; rather, it extends to all functionally equivalent structures, methods, and uses, such as are within the scope of the appended claims.

What is claimed:

1. A MEG recovery vessel including:
    an inlet in fluid communication with a MEG stream exiting a MEG treatment, the MEG stream having a first pH level;
    a port in fluid communication with a gas stream, the gas stream containing more than 50% $CO_2$;
    an outlet for the MEG stream after contact with the gas stream; and
    a vent for the gas stream after contact with the MEG stream;
    wherein the MEG stream after contact with the gas stream has a second pH level lower than the first pH level; and
    wherein the gas stream after contact with the MEG stream has a lowered $CO_2$ content.

2. A MEG recovery vessel according to claim 1 wherein an amount of $CO_2$ in the gas stream is at least equal to a stoichiometric quantity effective for achieving a reduced pH level of the MEG stream.

3. A MEG recovery vessel according to claim 1 wherein an amount of $CO_2$ in the gas stream is greater than a stoichiometric quantity effective for achieving a reduced pH level of the MEG stream.

4. A MEG recovery system according to claim 1 wherein the second lower pH level is at least 6.

5. A MEG recovery vessel according to claim 1 wherein the second lower pH level is 7.

6. A MEG recovery vessel according to claim 1 wherein the MEG stream is mixed with a second MEG stream having a different pH level than the first pH level.

7. A MEG recovery vessel according to claim 6 wherein the different pH level is 7.

8. A MEG recovery vessel according to claim 1 wherein the MEG stream is mixed with a second MEG stream having a different salt content than that of the MEG stream.

9. A MEG recovery vessel according to claim 1 wherein the MEG treatment includes a MEG regeneration unit.

10. A MEG recovery vessel according to claim 1 wherein the gas stream is from a MEG reclamation unit.

11. A MEG recovery vessel according to claim 1 wherein the MEG treatment lowers a non-MEG content of a mixture containing the MEG stream.

12. A MEG recovery gas/liquid contactor vessel comprising:
    an inlet in fluid communication with a MEG stream exiting a MEG treatment;
    a port in fluid communication with a gas stream containing more than 50% $CO_2$;
    an outlet for a reduced pH MEG stream; and
    a different outlet to vent a reduced $CO_2$ gas stream;
    wherein the MEG stream and the gas stream come into contact with one another within the gas/liquid contactor vessel.

13. A method for pH control of a MEG stream, the method comprising:
    contacting a MEG stream with a gas stream, the MEG stream being from a MEG treatment, the gas stream containing more than 50% $CO_2$.

14. A method according to claim 13 wherein an amount of $CO_2$ in the gas stream is at least equal to a stoichiometric quantity effective for achieving a reduced pH level of the MEG stream.

15. A method according to claim 13 wherein an amount of $CO_2$ in the gas stream is a stoichiometric quantity effective for achieving a reduced pH level of the MEG stream.

16. A method according to claim 13 further comprising mixing the MEG stream with a second MEG stream having a different pH level than that of the MEG stream.

17. A method according to claim 13 further comprising mixing the MEG stream with a second MEG stream having a different salt content than that of the MEG stream.

18. A method according to claim 13 wherein a pH level the MEG stream is at least 6 after contact with the gas stream.

19. A method according to claim 13 wherein the MEG treatment includes a MEG regeneration unit.

20. A method according to claim 13 wherein the gas stream is from a MEG reclamation unit.

21. A method according to claim 13 wherein the MEG treatment lowers a non-MEG content of a mixture containing the MEG stream.

* * * * *